United States Patent
Tseng et al.

(10) Patent No.: US 9,489,330 B2
(45) Date of Patent: Nov. 8, 2016

(54) SENSING SYSTEM, ELECTRONIC DEVICE AND SENSING METHOD

(71) Applicant: Acer Incorporated, New Taipei (TW)

(72) Inventors: Kai-Lun Tseng, New Taipei (TW); Ching-Piao Kuan, New Taipei (TW)

(73) Assignee: Acer Incorporated, New Taipei (TW)

( * ) Notice: Subject to any disclaimer, the term of this patent is extended or adjusted under 35 U.S.C. 154(b) by 466 days.

(21) Appl. No.: 14/195,872

(22) Filed: Mar. 4, 2014

(65) Prior Publication Data

US 2015/0157230 A1 Jun. 11, 2015

(30) Foreign Application Priority Data

Dec. 11, 2013 (TW) .............................. 102145611 A

(51) Int. Cl.
*A61B 5/00* (2006.01)
*G06F 13/38* (2006.01)

(52) U.S. Cl.
CPC ........... *G06F 13/385* (2013.01); *A61B 5/6898* (2013.01); *A61B 2560/045* (2013.01)

(58) Field of Classification Search
CPC combination set(s) only.
See application file for complete search history.

(56) References Cited

U.S. PATENT DOCUMENTS

2005/0165323 A1* 7/2005 Montgomery et al. ....... 600/544

FOREIGN PATENT DOCUMENTS

TW 201303739 1/2013
TW M452404 5/2013

* cited by examiner

*Primary Examiner* — Huan Tran
(74) *Attorney, Agent, or Firm* — Jianq Chyun IP Office

(57) ABSTRACT

A sensing system is provided. The system includes an electronic device and a detachable sensor. The detachable sensor could be connected to the electronic device through a connecting interface. When the electronic device detects that the detachable sensor is connected to the electronic device, the electronic device obtains a plurality of sensing data, and transforms the sensing data into a plurality of sensing results. Also, when the electronic device is connected to a host device, the electronic device sends the sensing results to the host device.

18 Claims, 2 Drawing Sheets

SENSING SYSTEM, ELECTRONIC DEVICE AND SENSING METHOD

CROSS-REFERENCE TO RELATED APPLICATION

This application claims the priority benefit of Taiwan application serial no. 102145611, filed on Dec. 11, 2013. The entirety of the above-mentioned patent application is hereby incorporated by reference herein and made a part of this specification.

BACKGROUND

1. Field of the Invention

The invention is directed to a communication system and more particularly, to a sensing system, an electronic device in the sensing system and sensing method.

2. Description of Related Art

With the progressive development of technologies, mobile electronic devices such as smart phones or tablet computers are widely used. On the other hand, various types of sensors such as motion sensor, pressure gauges, ambient light sensors (ALS) or even electrocardiography (ECG) sensors are widely applied in people's daily life.

Generally, a part of the sensors, such as a motion sensor, are disposed in an electronic device, such that sensing results can be directly processed and used in the mobile electronic device. However, due to concerns with respect to the size and power consumption of the mobile electronic device, not all the sensors required by a user can be installed in the mobile electronic device. Moreover, when being operated by a user, the electronic device can not be tightly connected to the user any time, and even if the ECG sensor and/or any other sensor for sensing physical states is installed in the mobile electronic device, the sensors also can not completely present the sensing results.

SUMMARY

The invention provides a sensing system, an electronic device and a sensing method capable of sensing different objects by changing detachable sensors of the electronic device.

The invention is directed to a sensing system, including an electronic device and a first detachable sensor. The first detachable sensor is connected to the electronic device through a connecting interface. When detecting that the first detachable sensor is connected to the electronic device, the electronic device obtains a plurality of first sensing data through the first detachable sensor and transforms the first sensing data into a plurality of first sensing results. When being connected to a host device, the electronic device sends the first sensing results to the host device.

The invention is directed to an electronic device, including a communication unit, a processing unit and a connecting interface. The processing unit is coupled to the communication unit. The connecting interface is coupled to the processing unit. The processing unit detects whether a first detachable sensor is connected to the processing unit through the connecting interface, when detecting that the first detachable sensor is connected to the processing unit, the processing unit obtains a plurality of first sensing data through the first detachable sensor and transforms the first sensing data into a plurality of first sensing results, and when being connected to a host device through the communication unit, the processing unit sends the first sensing results to the host device through the communication unit.

The invention is directed to a sensing method adapted for an electronic device in a sensing system, which includes the following steps. First, whether a first detachable sensor is connected is detected. Then, when detecting that the first detachable sensor is connected to, a plurality of first sensing data is obtained through the first detachable sensor and the first sensing data is transformed into a plurality of first sensing results. Thereafter, when a host device is connected to, the first sensing results are sent to the host device.

To sum up, the invention provides a sensing system, an electronic device and a sensing method thereof capable of obtaining sensing data through detachable sensors and after the electronic device is connected to a host device, the sensing results obtained by transforming the sensing data can be sent to the host device.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
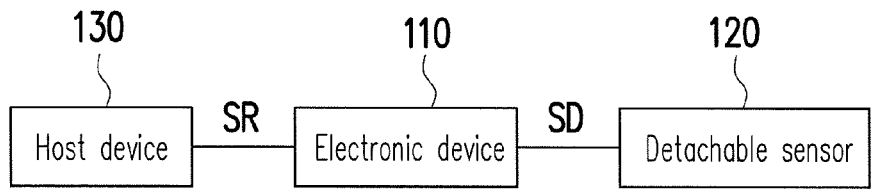
FIG. 1 is a system block diagram illustrating a sensing system according to an embodiment of the invention.

FIG. 1 is a system block diagram illustrating a sensing system according to an embodiment of the invention. With reference to FIG. 1, a sensing system 10 includes an electronic device 110, a detachable sensor 120 and a host device 130. The detachable sensor 120 is connected to the electronic device 110 through a connecting interface of the electronic device 110. When detecting that the detachable sensor 120 is connected to the electronic device 110, the electronic device 110 obtains a plurality of sensing data SD through the detachable sensor 120 and transforms the sensing data SD into a plurality of sensing results SR. When being connected to the host device 130, the electronic device 120 sends the sensing results SR to the host device 130.

To be brief, in the present embodiment, the host device 130 may be an electronic device, such as a smart phone, a tablet computer, notebook computer, a personal computer or the like. The electronic device 120 attached to the host device 130 may be collectively considered as a mobile electronic device for a user to operate and carry easily. Additionally, the electronic device 120 may be a wearable electronic device for the user to wear. The connecting interface of the electronic device 110 may be a physical connection port, such that the detachable sensor 120 may be connected to the electronic device 110 through the physical connection port and fixed to the electronic device 110.

The detachable sensor 120 may be any one of sensors for sensing different objects, such as a motion sensor, an ambient light sensor (ALS), a thermometer, a altimeter, a pressure gauge, a microphone, a global positioning system (GPS) locator, a proximity sensor, or even an electrocardiography (ECG) sensor, an electroencephalogram sensor or the like, which may be plugged in and out or replaced by the user to sense a sensing object corresponding to the detachable sensor 120.

On the other hand, the electronic device 110 may also include an embedded sensor. The electronic device 110 may obtain the other sensing data through the embedded sensor, such that the electronic device 110 may calculate in a fusion manner according to the sensing data SD obtained through the detachable sensor 120 and the other sensing data obtained through the embedded sensor to generate the sensing results SR. For instance, the electronic device 110 may include a motion sensor (which is composed of, for example, a gyroscope, an accelerometer and a magnetic sensor). The motion sensor may be served as the embedded sensor and when being connected to a GPS locator (which is an implementation of the detachable sensor 120) through the connecting interface, the electronic device 110 may calculate by utilizing a plurality of location data (e.g., the sensing data SD) obtained through the GPS locator and motion sensing data returned by the embedded sensor to generate and send location data (i.e., the sensing results SR) that is more accurate to the host device 130.

Generally, in the present embodiment, when being connected to the detachable sensor 120 (e.g., any one of the aforementioned sensors) through the connecting interface (e.g., the physical connection port), the electronic device 110 obtains the sensed sensing data SD through the detachable sensor 120 and transforms the sensing data SD into sensing results SR. The electronic device 110 send the sensing results SR to the host device 130 when being connected to the host device 130, such that the host device 130 may analyze or use the sensing results SR.

The electronic device 110 may be connected to the host device 130 via a wired (e.g., via the connecting interface complying with the universal serial bus (USB) standard) or a wireless manner (e.g., by switching radio frequency (RF) signals complying with the Bluetooth or the Wireless Fidelity (WiFi) standard, but the invention is not limited thereto. When being connected to the host device 130 via the wireless manner, the electronic device 110 may be set to be periodically connected to and/or disconnected from the host device 130, or the user may manually operate the electronic device 110 or the host device 130 for the connection.

In another embodiment, the electronic device 110 may also be switched to a control mode (e.g., by the use clicking on the electronic device 110, or by the host device 130 receiving a control signal corresponding to an operation of switching to the control mode. During the mode switching, the electronic device 110 maintains the connection with the host device 130 and immediately returns the sensing results SR (which is calculated and generated according to the sensing data SD obtained through the detachable sensor 120 and/or the other sensing data obtained through the embedded sensor) to the host device 130. For example, when the detachable sensor 120 (or the embedded sensor) connected to the electronic device 120 is a motion sensor, the user may perform an operation corresponding to a mouse or a gesture by moving the electronic device 120 when the electronic device is switched to the control mode, but the invention is not limited thereto.

Figure 2:
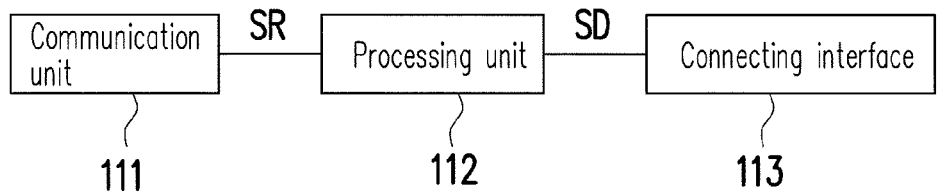
FIG. 2 is a device block diagram illustrating an electronic device according to an embodiment of the invention.

FIG. 2 is a device block diagram illustrating an electronic device according to an embodiment of the invention. With reference to FIG. 2, the electronic device 110 includes a communication unit 111, a processing unit 112 and a connecting interface 113. The processing unit 112 is coupled to the communication unit 111. The connecting interface 113 is coupled to the processing unit 112. The processing unit 112 detects whether a detachable sensor (e.g., the detachable sensor 120 illustrated in FIG. 1) is connected to the processing unit 112 through the connecting interface 113. When detecting that the detachable sensor is connected to the processing unit 112 through the connecting interface 113, the processing unit 112 obtains a plurality of sensing data SD through the detachable sensor and transforms the sensing data SD into a plurality of sensing results SR. When being connected to a host device (e.g., the host device 130 illustrated in FIG. 1) through the communication unit 111, the processing unit 112 sends the sensing results SR to the host device through the communication unit 111.

It is to be mentioned that the electronic device 110 may be connected to the host device 130 via a wired or a wireless manner. When the electronic device 110 is connected to the host device 130 via a wired manner, the communication unit 111 is a connecting interface with a physical connection port, such as a USB connection port. If the electronic device 110 is connected to the host device 130 via a wireless manner, the communication unit 111 may be an RF signal processing unit for receiving/sending RF signals complying with the Bluetooth or the WiFi standard.

In an embodiment of the invention, the electronic device 110 further includes an embedded sensor. The processing unit 112 may solely obtain the sensing data SD through the embedded sensor and transforms the sensing data SD into the sensing results SR, or alternatively, the processing unit 112 may also calculate according to the sensing data SD obtained from the embedded sensor and the sensing data SD obtained from the detachable sensor connected through the connecting interface 113 to generate the sensing results SR.

Moreover, in an embodiment of the invention, the electronic device 110 further includes a storage unit. When detecting that a detachable sensor (i.e., a first detachable sensor) is removed from the connecting interface 113, and another detachable sensor (i.e., a second detachable sensor) is connected to the processing unit 112, the processing unit 112 may store sensing data SD (i.e. first sensing data) which is obtained through the first detachable sensor or sensing results SR (i.e., first sensing results) which are calculated according to the first sensing data but not yet sent to the host device in the storage unit for backup. The processing unit 112 continue to obtain sensing data SD (i.e., second sensing data) through the second detachable sensor and transforms the sensing data SD into sensing results SR (i.e., second sensing results), and so on.

Figure 3:
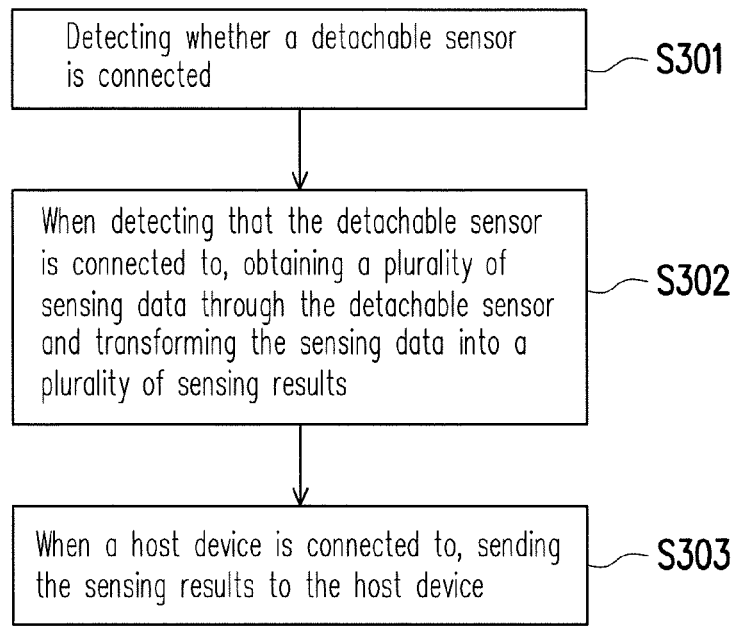
FIG. 3 is a flowchart of a sensing method according to an embodiment of the invention.

The invention also provided a sensing method, adapted for an electronic device (e.g., the electronic device 110 illustrated in FIG. 1 and FIG. 2) of a sensing system (e.g., the sensing system 10 illustrated in FIG. 1). FIG. 3 is a flowchart of a sensing method according to an embodiment of the invention. With reference to FIG. 3, first, in step S301, whether a detachable sensor is connected to is detected. Then, in step S302, when detecting that the detachable sensor is connected to, a plurality of sensing data is obtained through the detachable sensor, and the sensing data is transformed into a plurality of sensing results. Next, in step S303, when a host device (e.g., the host device 130 illustrated in FIG. 1) is connected to, the sensing results are sent to the host device.

Figure 4:
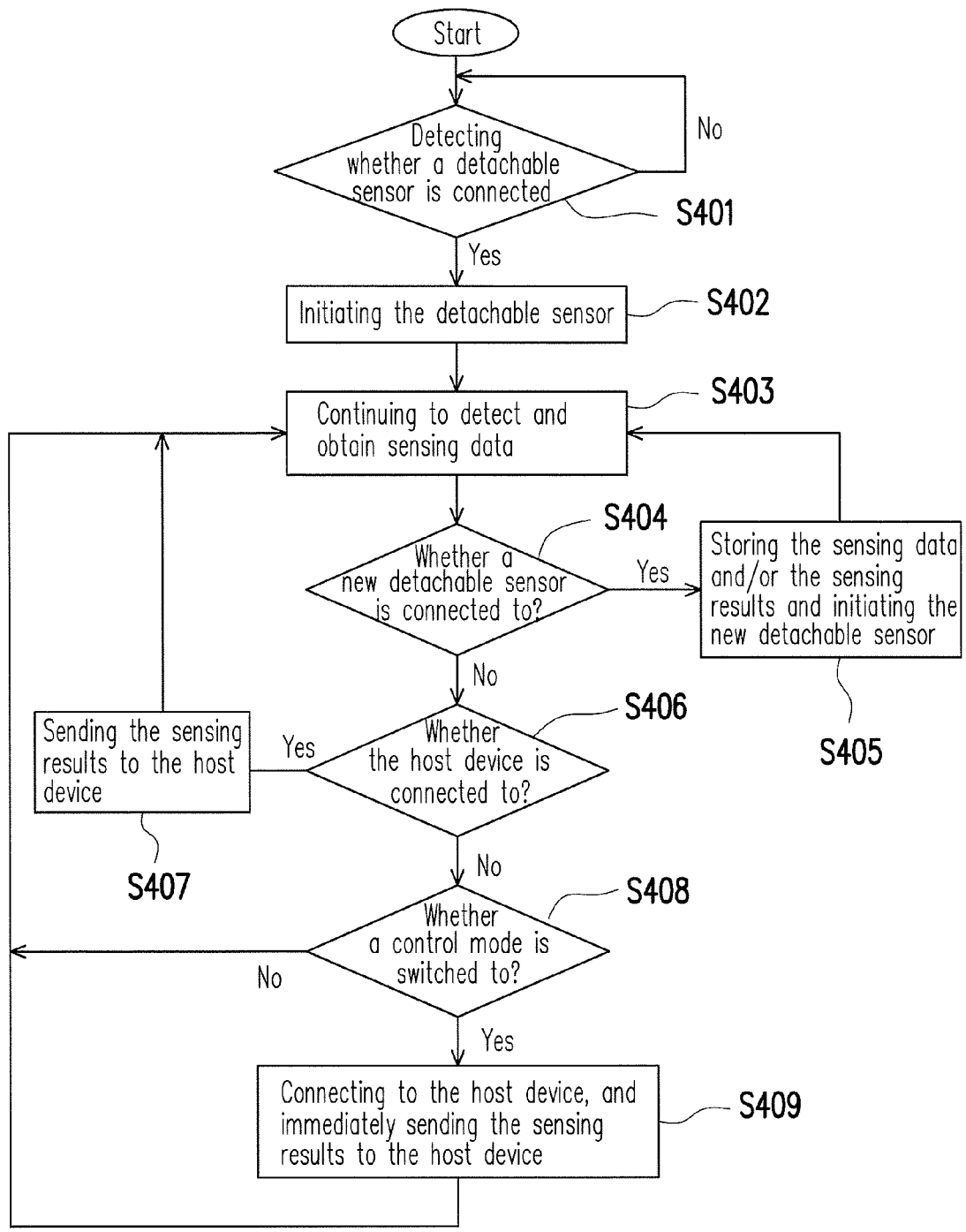
FIG. 4 is a flowchart of a sensing method according to an embodiment of the invention.

FIG. 4 is a flowchart of a sensing method according to an embodiment of the invention. In comparison with the embodiment illustrated in FIG. 3, the embodiment illustrated in FIG. 4 includes steps that are more detailed. With reference to FIG. 2 and FIG. 4, the processing unit 112 first detects whether a detachable sensor (e.g., the first detachable sensor) is connected to through a connecting interface (step S401). When detecting that detachable sensor is connected to through the connecting interface 113 (step S401, yes), the processing unit 112 initiates the detachable sensor by, for example, supplying power to the detachable sensor through the connecting interface 113 and initiating functions in the processing unit 112 that are corresponding to the detachable sensor (step S402). After the initiation step, the processing unit 112 continues to detect and obtain sensing data SD through the detachable sensor and generate sensing results SR according to the sensing data SD (step S403).

The processing unit 112 further continues to detect whether the detachable sensor is disconnected therefrom and to be connected to a new detachable sensor (e.g., the second detachable sensor) through the connecting interface 113 (step S404). When detecting that the processing unit 112 is connected to the new detachable sensor through the connecting interface (step S404, yes), the processing unit 112 stores sensing data SD which is not yet transformed into the sensing results and/or sensing results SR which are not yet sent to the host device in a storage unit (not shown) of the electronic device 110 and initiates the newly connected detachable sensor (step S405). After the initiation of the new detachable sensor is completed, the processing unit 112 continues to obtain the sensing data SD through the new detachable sensor (step S403).

On the other hand, the processing unit 112 continues to determine whether the host device is connected to (step S406). When determining that the host device is connected to (step S406, yes), the processing unit 112 sends the sensing results SR to the host device (step S407). After sending the sensing results SR to the host device, the processing unit 112 continues to detect and obtain the sensing data SD.

Thereafter, the processing unit 112 further determines whether the electronic device 110 is switched to a control mode due to receiving a control message from the host device or an operation signal by the user operating the electronic device 110 (step S408). When determining that the electronic device 110 is not switched to the control mode (step S408, no), the processing unit 112 continues to obtain the sensing data SD through the detachable sensor. When determining that the electronic device 110 is switched to the control mode (step S408, yes), the processing unit 112 establishes connection with the host device, and maintains the connection and immediately sends the sensing results SR to the host device (step S409). It is to be noted that step S409 and the connection operation with the host device may be performed only when the electronic device 110 is connected to the host device in the wireless manner, for example, the processing unit 112 may be actively paired with the host device through the communication unit 111 by using the Bluetooth communication and then sends the sensing results SR, but the invention is not limited thereto.

The sequence for performing step S404, S406 and S408 may be changed according to the actual implementation. Additionally, in a scenario where the electronic device 110 further includes an embedded sensor, the processing unit 112 may enable the embedded sensor as needed to obtain corresponding sensing data. For example, when determining that the detachable sensor is not connected to, the processing unit 112 may enable the embedded sensor to obtain the sensing data SD. Alternatively, when determining that an object detected by the currently connected embedded sensor is associated with an object detected by the detachable sensor (such as a scenario where the embedded sensor is a motion sensor, and the detachable sensor is a GPS locator, or alternatively the embedded sensor is a motion sensor and the detachable sensor is an ECG recorder), the processing unit 112 may also enable the embedded sensor to calculate according to the sensing data SD obtained through the embedded sensor and the sensing data SD obtained through the detachable sensor to generate the sensing results SR, which constructs no limitations to the invention.

In light of the foregoing, the invention provides a sensing system, an electronic device of the sensing system and a sensing method thereof, in which different detachable sensors are connected to detect different objects, the sensing data is transformed into data (the aforementioned sensing results) that can be utilized by the host device (e.g., a mobile electronic device) of the sensing system. For example, the detachable sensor may be an ECG recorder or a thermometer, and the electronic device is wearable electronic device, the electronic device may be worn by the user to immediately record physical states of the user and immediately returns the recorded physical states to the host device. Thereby, when any abnormality occurs to the physical states of the user, proper treatment may be immediately performed, such as by sending a warning message, sending a warning message to one or more specific persons dialing to a predetermined telephone number.

In one of the embodiments of the invention, the electronic device further includes an embedded sensor, which can be used alone. For example, the embedded sensor is a motion sensor, and when being operated with the electronic device switched to a control mode, the electronic device may be served as a wireless mouse, an air gesture or a joystick. The electronic device may be used together with the detachable sensor when an object detected by the embedded sensor is associated with an object detected by the detachable sensor, such that the sensing results calculated and generated by the electronic device can be more accurate.

Although the invention has been described with reference to the above embodiments, it will be apparent to one of the ordinary skill in the art that modifications to the described embodiment may be made without departing from the spirit of the invention. Accordingly, the scope of the invention will be defined by the attached claims not by the above detailed descriptions.

What is claimed is:

1. A sensing system, comprising:
   an electronic device; and
   a first detachable sensor, connected to the electronic device through a connecting interface, wherein
   when detecting that the first detachable sensor is connected to the electronic device, the electronic device obtains a plurality of first sensing data through the first detachable sensor and transforms the first sensing data into a plurality of first sensing results, and
   when being connected to a host device, the electronic device sends the first sensing results to the host device.

2. The sensing system according to claim 1, further comprising:
   a second detachable sensor, connected to the electronic device through the connecting interface, wherein
   when the electronic device detects that the first detachable sensor is disconnected from the electronic device, and the second detachable sensor is connected to the electronic device, the electronic device stores the first sensing data, obtains a plurality of second sensing data through the second detachable sensor and transforms the second sensing data into a plurality of second sensing results, and when being connected to the host device, the electronic device sends the second sensing results to the host device.

3. The sensing system according to claim 1, wherein when receiving an operation signal, the electronic device is connected to the host device and immediately returns the first sensing results to the host device.

4. The sensing system according to claim 1, wherein when receiving a control message from the host device, the electronic device immediately returns the first sensing results to the host device.

5. The sensing system according to claim 1, wherein the electronic device comprises an embedded sensor, wherein the electronic device obtains a plurality of third sensing data through the embedded sensor and transforms the third sensing data into a plurality of third sensing results, when being connected to the host device, the electronic device sends the third sensing results to the host device, and an object sensed by the embedded sensor is different from an object sensed by the first detachable sensor.

6. The sensing system according to claim 5, wherein the electronic device calculates according to the first sensing data and the third sensing data to generate a plurality of fourth sensing results and sends the fourth sensing results to the host device.

7. An electronic device, comprising:
a communication unit;
a processing unit, coupled to the communication unit; and
a connecting interface, coupled to the processing unit, wherein the processing unit detects whether a first detachable sensor is connected to the processing unit through the connecting interface, when detecting that the first detachable sensor is connected to the processing unit, the processing unit obtains a plurality of first sensing data through the first detachable sensor and transforms the first sensing data into a plurality of first sensing results, and when being connected to a host device through the communication unit, the processing unit sends the first sensing results to the host device through the communication unit.

8. The electronic device according to claim 7, wherein when detecting that the first detachable sensor is connected to the electronic device, and a second detachable sensor is connected to the processing unit through the connecting interface, the processing unit stores the first sensing data, obtains a plurality of second sensing data through the second detachable sensor and transforms the second sensing data into a plurality of second sensing results, and when being connected to the host device through the communication unit, the processing unit sends the second sensing results to the host device.

9. The electronic device according to claim 7, wherein when receiving an operation signal, the processing unit is connected to the host device through the communication unit and immediately returns the first sensing results to the host device.

10. The electronic device according to claim 7, wherein when receiving a control message from the host device through the communication unit, the processing unit immediately returns the first sensing results to the host device.

11. The electronic device according to claim 7, further comprises:
an embedded sensor, coupled to the processing unit, wherein the processing unit obtains a plurality of third sensing data through the embedded sensor and transforms the third sensing data into a plurality of third sensing results, when being connected to the host device through the communication unit, the processing unit sends the third sensing results to the host device through the communication unit, and an object sensed by the embedded sensor is different from an object sensed by the first detachable sensor.

12. The electronic device according to claim 11, wherein the electronic device calculates according to the first sensing data and the third sensing data to generate a plurality of fourth sensing results and sends the fourth sensing results to the host device.

13. A sensing method, adapted for an electronic device in a sensing system, comprising:

detecting whether a first detachable sensor is connected;

when detecting that the first detachable sensor is connected to, obtaining a plurality of first sensing data through the first detachable sensor and transforming the first sensing data into a plurality of first sensing results; and when a host device is connected to, sending the first sensing results to the host device.

14. The sensing method according to claim 13, wherein after the step of detecting that the first detachable sensor is connected to, the method further comprises:

when detecting that the first detachable sensor is disconnected from, and a second detachable sensor is connected to, storing the first sensing data, obtaining a plurality of second sensing data through the second detachable sensor and transforming the second sensing data into a plurality of second sensing results, and when the host device is connected to, sending the second sensing results to the host device.

15. The sensing method according to claim 13, further comprising:

when receiving an operation signal, connecting to the host device and returning the first sensing results to the host device.

16. The sensing method according to claim 13, further comprising:

when receiving a control message from the host device, immediately returning the first sensing results to the host device.

17. The sensing method according to claim 13, further comprising:

obtaining a plurality of third sensing data through an embedded sensor and transforming the third sensing data into a plurality of third sensing results; and when being connected to the host device, transmitting the third sensing results to the host device, wherein an object sensed by the embedded sensor is different from an object sensed by the first detachable sensor.

18. The sensing method according to claim 17, wherein before the step of obtaining the third sensing data through the embedded sensor, the method further comprises:

calculating according to the first sensing data and the third sensing data to generate a plurality of fourth sensing results and sending the fourth sensing results to the host device.

* * * * *